United States Patent [19]
Holladay et al.

[11] Patent Number: 5,709,218
[45] Date of Patent: Jan. 20, 1998

[54] METHOD OF PREDICTING VISUAL ACUITY WITH CHANGE OF SPHEROCYLINDRICAL REFRACTIVE ERROR

[75] Inventors: Jack T. Holladay, Belaire, Tex.; Alan J. Lang, Long Beach; Valdemar Portney, Tustin, both of Calif.

[73] Assignee: Allergan, Waco, Tex.

[21] Appl. No.: 631,150

[22] Filed: Apr. 15, 1996

[51] Int. Cl.⁶ ..................................................... A61B 13/00
[52] U.S. Cl. ........................................... 128/745; 351/246
[58] Field of Search ................................. 128/745, 898; 623/6; 351/246, 160–161, 177

[56] References Cited

U.S. PATENT DOCUMENTS 5,512,965  4/1996  Snook ....................................... 351/205

OTHER PUBLICATIONS

"The Influence of Astigmatism on the Response Functio of an Optical Sysetm" Proc. Roy Soc. Lon. Jan. 1956 pp. 91–104.

"The Relationship of Visual Acuity, Refractive Error, and Pupil Size, After Kerasotomy" Arch Opth vol. 109 Jan. 1991 pp. 70–76.

Primary Examiner—Francis Jaworski
Attorney, Agent, or Firm—Walter A. Hackler

[57] ABSTRACT

The present invention is directed to a method for predicting visual acuity to the subject due to change in spherocylindrical refractive error of the subject's eye utilizing measurements of uncorrected visual acuity, corrected visual acuity and spherical cylindrical refractive error. A defocus equivalent is calculated and predictions of uncorrected visual acuity is made through the use of a defocused acuity graph.

4 Claims, 3 Drawing Sheets

METHOD OF PREDICTING VISUAL ACUITY WITH CHANGE OF SPHEROCYLINDRICAL REFRACTIVE ERROR

The present invention generally relates to a method of predicting visual acuity in a subject due to a change in spherocylindrical refractive error.

The human eye is operative for providing vision by transmitting an image through a clear outer portion thereof called a cornea and focusing the incoming image through a lens onto a retina. The quality of the focused image, that is acuity, clarity, or clearness of vision depends upon numerous factors including the size and shape of the eye and the transparency of the cornea lens. With age vision deteriorates because of the diminished light which is transmitted to the retina through the lens due to cataractous tissue in the eye. To correct this condition, the lens is surgically removed and replaced with an artificial intraocular lens, IOL.

Surgically implanted IOLs have become the preferable correction mode in favor of contact lenses or glasses because they provide a permanent replacement for the removed lens.

Under the current practice, cataract removal and implantation of an IOL is generally performed in a single surgical procedure. An incision is provided to remove the cataract and the insertion of the IOLs.

The IOLs are manufactured with a range of corrective refractive polymers and it is most desirable to not only predict the visual acuity achieved by a given or selected IOL, but, therewith predict changes in visual acuity due to surgical procedures.

That is, prior to surgery it is desirable for a physician to determine which of a number of IOLs having different refractive characteristics should be utilized taking into account the incision size and placement of the IOL to achieve the best uncorrected visual acuity for the subject.

It should be appreciated that this procedure which determines the post operative refraction of the subject is difficult and heretofore inexact.

Typical procedures have involved a measurement of the axial length of the eye, measurement of corneal power and assume a lack of post operative induced stigmatism or spherical refractive changes in the cornea.

The problem of predicting visual acuity is further compounded by the post operative changes which may also change the refractive power needed for an IOL in a particular subject. For example, as a result of the differences in the manner in which the capture bag shrinks after surgical procedure, the surgical procedure itself, or the healing of the incision.

It is of course undesirable to perform a second surgical procedure to remove an IOL with an incorrect refractive index and replace it with a properly powered one particularly if the visual acuity of the subject can be predicted which would eliminate this secondary surgical procedure. Further, it should be appreciated that while spherical refractive error can be accommodated by a change along the actual length of the eye, cylindrical errors commonly occurring as a result of post operative stigmatism is not corrected in aphakic subjects (i.e. subjects with removed lenses).

The present invention provides for a method of predicting visual acuity of a subject due to a change in spherocylindrical refractive error. The method utilizes the knowledge of the subject's visual acuity associated with the initial spherocylindrical error and thus corrected visual acuity associated with zero refractive error. These parameters are commonly available in clinical testing and the method allows assessment of visual benefits from cataract and refractive procedures which modify the subject's spherocylindrical refractive error. The method can be used manually or programmed for use in a personal computer or the like.

SUMMARY OF THE INVENTION

A method in accordance with the present invention for predicting visual acuity of the subject due to a change in spherocylindrical refractive error of the subject's eye generally includes steps of measuring an uncorrected visual acuity of the subject's eye along with measuring a best corrected visual acuity of the subject eye.

Following the measurement of a spherocylindrical refractive error of the subject eye a spherocylindrical equivalent is calculated. The spherocylindrical refractive error is comprised of spherical error and cylindrical error and the spherocylindrical equivalent is defined as the optimum spherical refraction needed to correct for the spherocylindrical refractive error.

Thereafter a defocus equivalent is calculated from an absolute value of the spherical equivalent error and the cylindrical error.

From the value of the defocused acuity equivalent a pupil diameter is found through the use of the defocused acuity graph which corresponds to measured uncorrected visual acuity.

A new equivalent defocus is determined which may be the result of a change in surgical procedure on the subject's eye, insertion of an IOL in the subject's eye, or a change of the IOL in the subject's eye.

Upon the determination of the new equivalent defocus a predicted uncorrected visual acuity is found utilizing the defocused acuity graph which corresponds to determine pupil diameter and the new equivalent defocus.

In accordance with the present invention, the defocused acuity graph may be determined through the steps of measuring an uncorrected visual acuity in a plurality of subject eyes, measuring a best corrected visual acuity in each of the plurality of subject eyes and measuring a pupil diameter in each of the pluralities of subject eyes as well as measuring a spherocylindrical refractive error of each of the plurality of subject eyes.

Thereafter, a plurality of defocus equivalents corresponding to the different uncorrected visual acuities and pupil diameters are plotted to form a defocused acuity graph which is used in the method of the present invention.

The predicted uncorrected visual acuity is limited by the best corrected visual acuity and accordingly if the determination of the uncorrected visual acuity from the defocused acuity graph is greater than the best corrected visual acuity, than the predicted uncorrected visual acuity is equal to the best corrected visual acuity.

BRIEF DESCRIPTION OF THE DRAWINGS

The advantages and features of the present invention will be better understood by the following description when considered in conjunction with the accompanying drawings in which.

DETAILED DESCRIPTION

As reported by Jack T. Holladay, et al in the Archives of Ophthalmology, January 1991, Vol. 109, page 70, "The relationship of visual acuity, refractive error, and pupil size after radial keratotomy", early studies relating visual acuity and refractive error rarely considered the f-number of the eyes, and in some cases never mentioned the pupil diameter, resulting in a large amount of variability in their findings.

Later studies, however, reduced the variability by giving ambient light levels in patient age, for which an average pupil diameter could be determined. More recent studies did correct the pupil diameter, visual acuity, and refractive error and found a relationship between these parameters.

The article reports the results of twelve studies in which the refractive errors, visual acuities, and pupil diameters are tabulated to create a reference grid as shown in Table 1.

2. Calculation of Spherical Equivalent (Seq).

Spherical Equivalent is defined as the optimum spherical refraction needed to correct for spherocylindrical refraction error. In general form, Spherical Equivalent is defined as Seq=Fs [Sph, Cyl], where Fs is a function for spherical and cylindrical errors.

In the most simple form Seq=Sph+Cyl/2.

3. Calculation of Defocus Equivalent (Deq).

Defocus equivalent is proportional to the area of the blur circle formed by spherocylindrical refraction error. In general form, Defocus Equivalent is defined as:

Deq=Fd[Seq, Cyl], where Fd is a function of the absolute values of spherical equivalent and cylinder errors.

In the most simple form Deq=Seq+Cyl/2 (Ref. 1).

TABLE 1

SNELLEN VISUAL ACUITY AS A FUNCTION OF PUPIL SIZE AND DEFOCUS

| Defocus, | Pupil size, mm | | | | | | | | |
|---|---|---|---|---|---|---|---|---|---|
| Diopter | 0.5 | 1.0 | 2.0 | 3.0 | 4.0 | 5.0 | 6.0 | 7.0 | 8.0 |
| TDL* | 20/36 | 20/18 | 20/09 | 20/06 | 20/04 | 20/04 | 20/03 | 20/03 | 20/02 |
| 0.0 | 20/36 | 20/18 | 20/10 | 20/09 | 20/10 | 20/10 | 20/11 | 20/11 | 20/11 |
| 0.5 | 20/36 | 20/22 | 20/12 | 20/15 | 20/19 | 20/24 | 20/28 | 20/30 | 20/21 |
| 1.0 | 20/36 | 20/27 | 20/19 | 20/24 | 20/33 | 20/44 | 20/52 | 20/56 | 20/58 |
| 2.0 | 20/37 | 20/33 | 20/36 | 20/49 | 20/68 | 20/95 | 20/121 | 20/130 | 20/135 |
| 3.0 | 20/38 | 20/39 | 20/60 | 20/83 | 20/117 | 20/168 | 20/214 | 20/230 | 20/239 |
| 4.0 | 20/39 | 20/47 | 20/95 | 20/132 | 20/182 | 20/252 | 20/307 | 20/330 | 20/343 |
| 5.0 | 20/40 | 20/56 | 20/140 | 20/190 | 20/258 | 20/348 | 20/428 | 20/460 | 26/478 |

*TDL indicates theoretical diffraction limits

Figure 1:
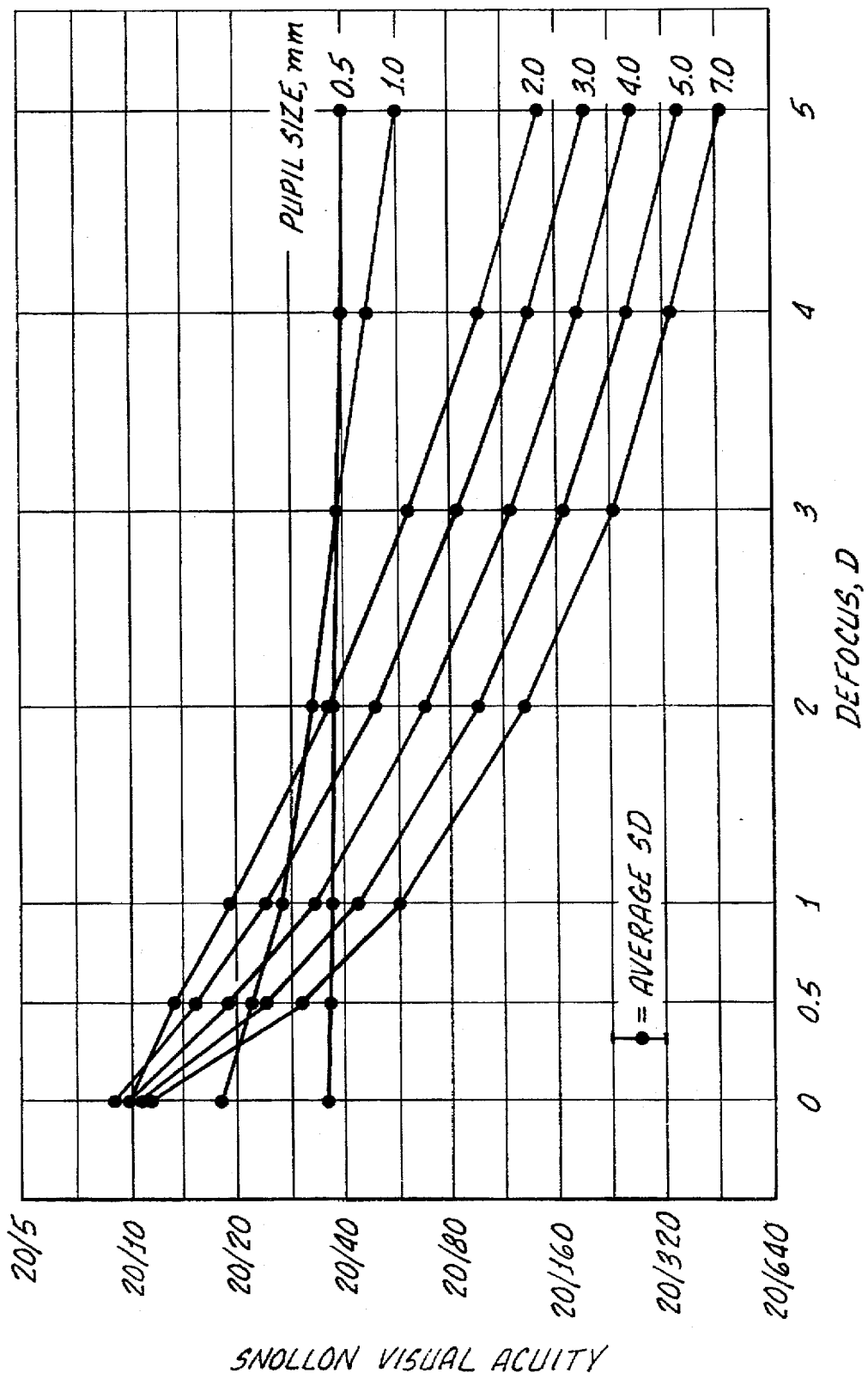
FIG. 1 is a plot of Snellens visual acuity versus diopters (D) defocus as a function of pupil diameter in normal eyes.

A plot of Table 1 which is a defocused acuity graph is shown in FIG. 1.

The defocused acuity graph as shown in FIG. 1 may be developed as part of the present invention or prior formulated defocused acuity graphs and may be utilized as one of the steps in accordance with the present invention.

As hereinabove noted, the present invention is directed to a method of predicting visual acuity of a subject due to a change in spherocylindrical refractive error. The method utilizes the knowledge of the subject's visual acuity associated with the initial spherical cylindrical error and best corrected visual acuity associated with zero refractive error. These primaries are commonly available in clinical testing. The method in accordance with the present invention allows assessment of visual benefits from cataract and refractive procedures which modify the subject's spherocylindrical refractive error and can be used in a manual mode or incorporated into a computer program for assisting in the needed calculations.

Basically the method in accordance with the present invention includes the following steps:

1. Measurement of three clinical parameters.

(1) Unaided or Uncorrected Visual Acuity (ucVA) which is a visual acuity measured without any refractive correction, such as contact lens or spectacles.

(2) Spherocylindrical refractive error of the subject (Rx). The refraction (Rx) consists of two components, Sph (sphere) and Cyl (cylinder). Spherical error can be corrected by a spherical lens and cylindrical error can be corrected by a cylindrical lens.

(3) Best Corrected Visual Acuity (ccVA) which is the visual acuity measured when the subject's refractive error is corrected by use of contacts or spectacles.

4. Determination of the unique Defocused Acuity Graph Fp describing the change in ucVA with Deq for a specific pupil size (P).

In general, ucVA=Fp[Deq;P], where Fp is a function of defocus equivalent and pupil sizes (P).

An example of the graphical representation of function Fp is shown in FIG. 1. The knowledge of ucVA and Deq defines a graph representing ucVA as a function of Deq for a given pupil size P.

5. Determination of the new Equivalent Defocus Deq due to a change in cataract or refractive procedure.

EXAMPLES a. New Deq due to optimization of the IOL surgeon constant in IOL power calculation.

The optimum surgeon constant for IOL power calculations (A-constant, etc.) is calculated from spherocylindrical errors from a group of subjects. The "optimum" is defined in statistical sense minimum standard deviation, etc. The use of the best IOL surgeon factor yields new set of spherical errors for the same group of subjects and, therefore, this would define new set of (Deq).

b. New Deq due to different surgical technique (reduction in incision size, incision location, etc.)

New set of cylinder errors is defined from the "predetermined database" of the induce cylinder due to surgical techniques (different incision sizes, different incision locations, etc.) and, therefore, this would define new defocus equivalent Deq.

6. Determination of new uncorrected visual acuity ucVA from the new defocus equivalent Deq.

New uncorrected visual acuity ucVA is defined from the established in Step 4 function Fp and new Defocus Equivalent value Deq.

7. Calculation of the predicted uncorrected visual acuity ucVAp.

Predicted uncorrected visual acuity is calculated form the following condition:

ucVAp=ucVA if ucVA<ccVA (best corrected visual acuity);

ucVAp=ccVA if ucVA≧ccVA.

Example 1

Figure 2:
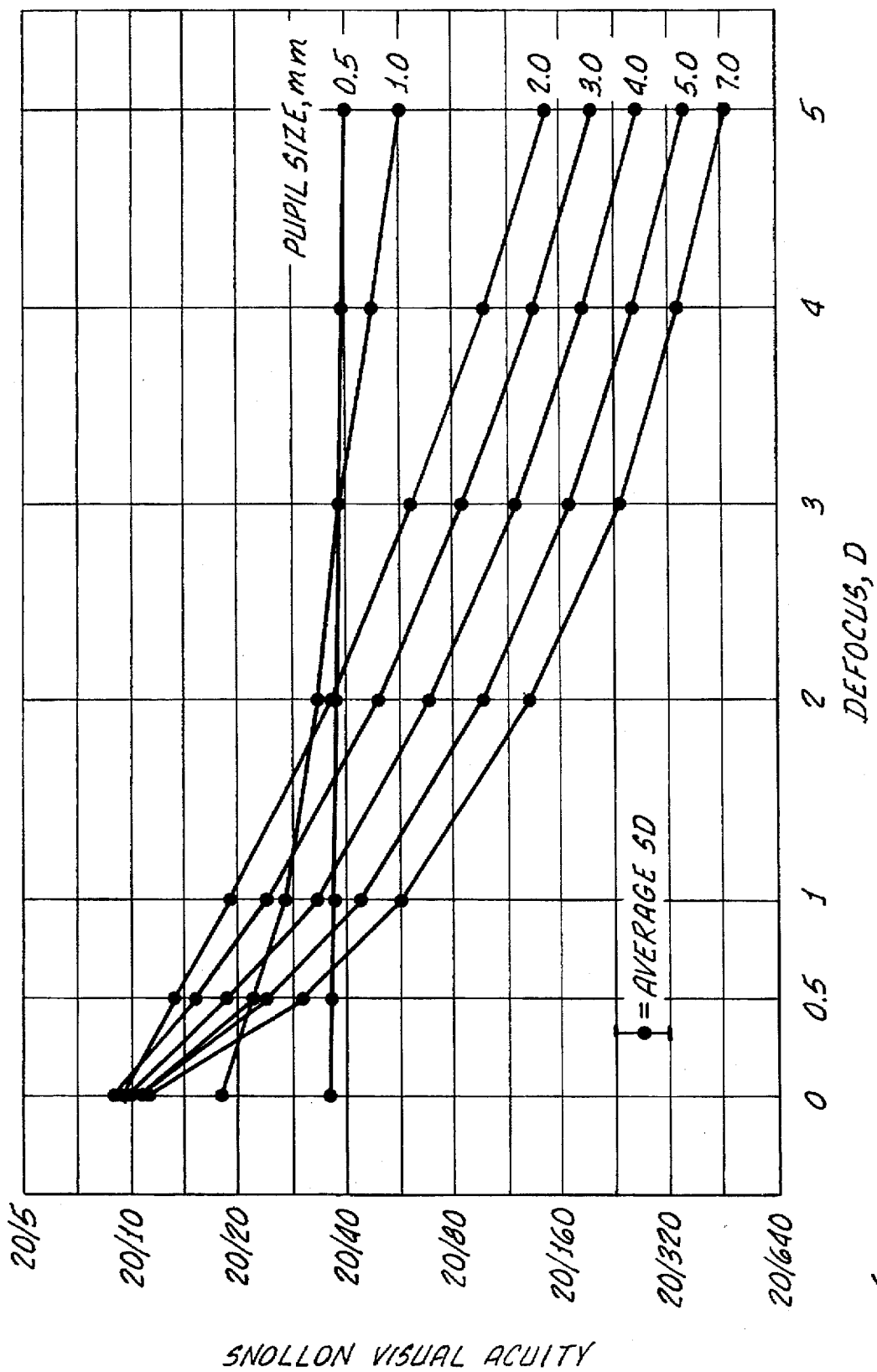
FIGS. 2 and 3 are the same as the plot shown in FIG. 1 illustrating the method in accordance with the present invention.

Optimization for IOL surgeon factor in IOL power calculation:

1. Sph=1 d, Cyl=1 D, ccVA=20/30, ucVA=20/50
2. Seq=1+(1)/2=1.5 D
3. Deq=1.5+(1)/2=2 D
4. The point (20/50, 2) falls onto the Defocus Graph, see x FIG. 2, corresponding to 3.3 mm diameter pupil.
5. Assume, new spherical error for a given subject equals 0 D due to optimization for IOL power. Then, new Deq=0.5 D.
6. New Deq=0.5 D corresponds to approximately ucVA= 20/20 from the Defocus Graph, see FIG. 2.
7. Predicted ucVAp=20/30 because ucVA>ccVA.

Example 2

New Surgical Technique

Figure 3:
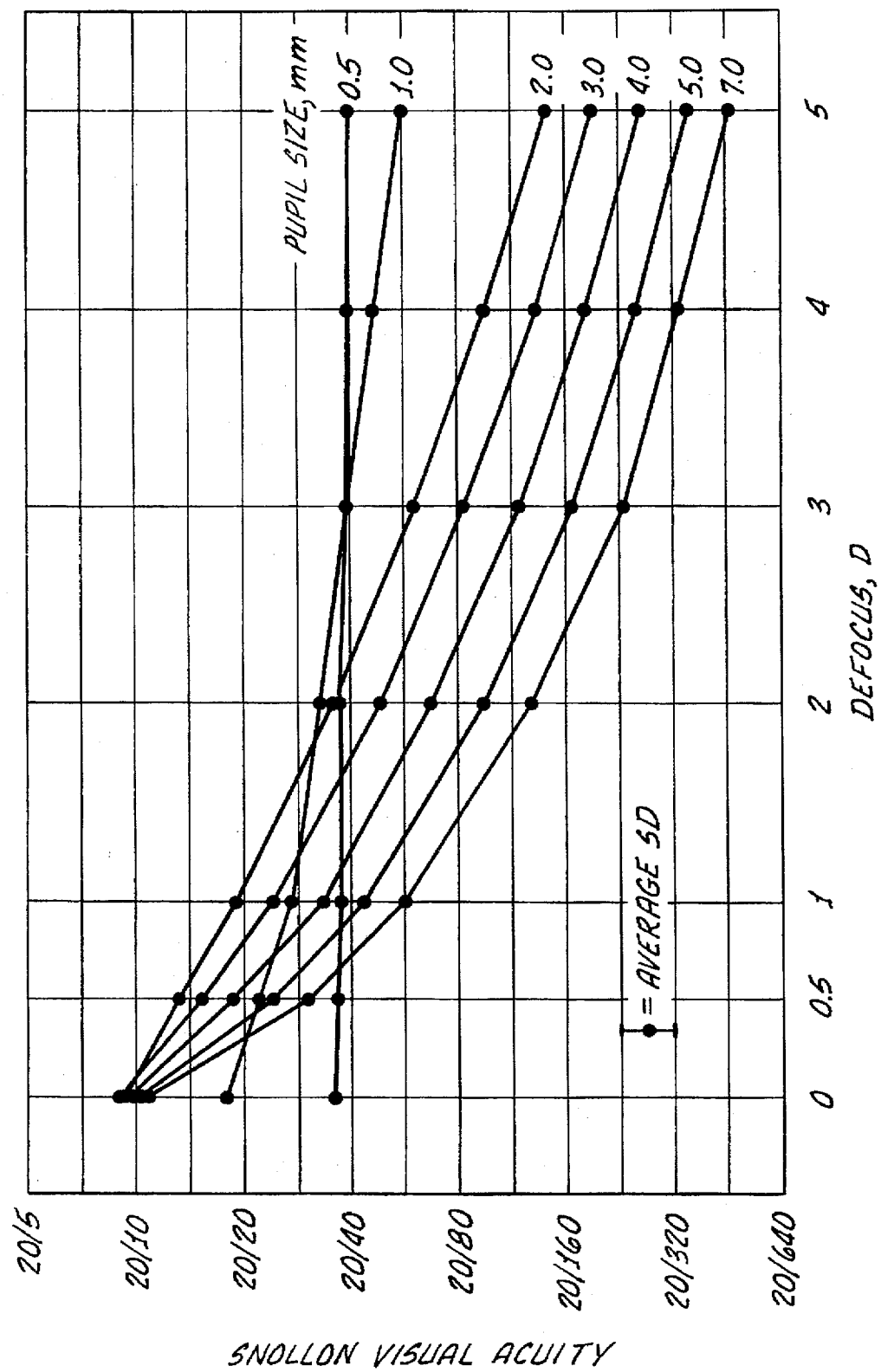

1. Sph=1 D, Cyl=1 D, ccVA=20/30, ucVA=20/50
2. Seq=1+(1)/2–1.5 D
3. Deq=1.5+*1)/2–2 D
4. The point (20/50, 2) falls onto Defocus Graph, see FIG. 3, corresponding to 3.3 mm diameter pupil.
5. Assume, new cylinder error for a given subject equals 0 D due to the use of IOL product which is inserted through small incision without inducing a corneal cylinder. Then, new Deq=1.5 D.
6. New Deq=1.5 corresponds to ucVA=20/35 from Defocus Graph, see FIG. 3.
7. Predicted ucVAp=20/35 because ucVA<ccVA Although there has been hereinabout described a specific method for predicting visual acuity of a subject due to change in spherocylindrical refractive error, the subject's eye in which the invention can be used to advantage, should be appreciated that the invention is not limited thereto. Accordingly, any and all modifications, variations, or equivalent arrangements which may occur to those skilled in the art should be considered within the scope of the present invention as defined in the appended claims.

What is claimed is:

1. A method for predicting visual acuity of a subject due to a change in spherocylindrical refractive error of the subject's eye, said method comprising the steps of:

measuring an uncorrected visual acuity, ucVA, of the subject's eye;

measuring a best corrected visual acuity, ccVA, of the subject's eye;

measuring a spherocylindrical refractive error, Rx, of the subject's eye, the spherocylindrical refractive error being comprised of spherical error and cylindrical error;

calculating a spherocylindrical equivalent, Seq., defined as the optimum spherical refraction needed to correct for the spherocylindrical refractive error;

calculating a defocus equivalent, Deq, from an absolute value of the spherical equivalent and cylindrical error;

determining from a Defocused Acuity Group a pupil diameter corresponding to the measured uncorrected visual acuity, ucVA, and the calculated defocus equivalent, Deq;

determining a new equivalent defocus Deq due to a change in surgical procedure on the subject's eye or insertion of an IOL in the subject's eye; or a change of IOL in the subject's eye; and determining from the Defocused Acuity Graph, a predicted uncorrected visual acuity, ucVA corresponding to the determined pupil diameter and the new equivalent defocus, Deq.

2. The method according to claim 1 wherein the step of determining a predicted uncorrected visual acuity, ucVA, includes comparing the predicted uncorrected visual acuity, ucVA, with the best corrected visual acuity, ccVA, if ucVA'≧ccVA then ucVA is assumed equal to ccVA.

3. A method for predicting visual acuity of a given subject due to a change in spherocylindrical refractive error of the given subject's eye, said method comprising the steps of:

measuring an uncorrected visual acuity, ucVA, in a plurality of subject eyes;

measuring a best corrected visual acuity, ccVA, in each of the plurality of subject eyes;

measuring a pupil diameter in each of the plurality of subject eyes;

measuring a spherocylindrical refractive error, Rx, of each of the plurality of subject eyes, the spherocylindrical being compared of spherical error and cylindrical error;

calculating a plurality of defocus equivalents, Deq, corresponding to different uncorrected visual acuities, ucVA, and pupil diameters, said defocus equivalents, Deq, being an absolute value of the spherical equivalent error and cylindrical error;

forming a Defocused Acuity Graph from the calculated defocus equivalents, uncorrected visual acuities and pupil diameter;

measuring an uncorrected visual acuity, ucVA, of the given subject's eye;

measuring a best corrected visual acuity, ccVA, of the given subject's eye;

measuring a spherocylindrical refractive error, Rx, of the given subject's eye, the spherocylindrical refractive error being comprised of spherical error and cylindrical error;

calculating a spherocylindrical equivalent, Seq., defined as the optimum spherical refraction needed to correct for the spherocylindrical refractive error of the given subject's eye;

determining from the Defocused Acuity Graph, a pupil diameter corresponding to the measured uncorrected visual acuity, ucVA, and the calculated defocus equivalent, Deq;

determining a new equivalent defocus Deq due to a change in surgical procedure on the subject's eye or insertion of an IOL in the subject's eye; or a change of IOL in the subject's eye; and determining from the Defocused Acuity Graph, a predicted uncorrected visual acuity, ucVA, corresponding to the determined pupil diameter and the new equivalent defocus, Deq.

4. The method according to claim 3 wherein the step of determining a predicted uncorrected visual acuity, ucVA, includes comparing the predicted uncorrected visual acuity, ucVA, with the best corrected visual acuity, ccVA, if ucVA≧ccVA then ucVA is assumed equal to ccVA.

* * * * *